United States Patent
Narizuka et al.

(10) Patent No.: US 6,331,649 B1
(45) Date of Patent: Dec. 18, 2001

(54) PROCESS FOR PRODUCING TRIFLUOROMETHYLBENZYLAMINES

(75) Inventors: Satoru Narizuka; Yutaka Katsuhara, both of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/532,004

(22) Filed: Mar. 21, 2000

(30) Foreign Application Priority Data

Mar. 23, 1999 (JP) .................................................. 11-078397

(51) Int. Cl.⁷ .................................................. C07C 211/00
(52) U.S. Cl. ...................... 564/384; 564/385; 564/397; 564/398; 564/407
(58) Field of Search ................................. 564/397, 398, 564/407, 384, 385

(56) References Cited

PUBLICATIONS

Freifelder et al., "Preparation of Isomeric Trifluoromethyl-benzylamines", J. Pharm. Sci. 54, May 1965, p. 1204.
Meindl et al., "Benzylamines: Synthesis and Evaluation of Antimycobacterial Properties", J. Med. Chem. 27, 1984, pp. 1111–1118.

*Primary Examiner*—Samuel Barts
(74) *Attorney, Agent, or Firm*—Crowell & Moring LLP

(57) ABSTRACT

The present invention relates to a process for producing a trifluoromethylbenzylamine represented by the general formula (1). This process includes the step of reducing an oxime represented by the general formula (2),

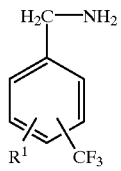
(1)

where $R^1$ represents hydrogen atom, a halogen atom selected from the group consisting of fluorine, chlorine, bromine and iodine, or trifluoromethyl group,

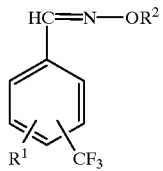
(2)

where $R^1$ is defined as above, and $R^2$ represents hydrogen atom, an alkyl group or an aralkyl group. With this process, the trifluoromethylbenzylamine can be produced with high selectivity.

13 Claims, No Drawings

PROCESS FOR PRODUCING TRIFLUOROMETHYLBENZYLAMINES

BACKGROUND OF THE INVENTION

The present invention relates to a process for producing trifluoromethylbenzylamines.

Trifluoromethylbenzylamines represented by the general formula (1) are important compounds, for example, as intermediates for producing medicines and agricultural chemicals.

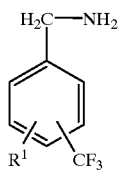
(1)

J. Pharm. Sci., 54, 1204 (1965) discloses a process for producing a trifluoromethylbenzylamine by a catalytic reduction of trifluoromethylbenzonitrile in the presence of a catalyst. J. Med. Chem., 27, 1111 (1984) discloses a process for producing a trifluoromethylbenzylamine by reducing a trifluoromethylbenzaldehyde oxime using a lithium aluminum hydride.

In the above-mentioned conventional processes, since the former process uses a large amount of catalyst while not being satisfactory in terms of yield, and the latter process involves the use of hazardous substances requiring non-aqueous conditions while also not achieving a high yield, both of these processes have not been able to achieve satisfactory results as production processes applied on an industrial scale.

SUMMARY OF THE INVENTION

It is therefore an object of the present invention to provide a process for producing a trifluoromethylbenzylamine with high yield.

According to the present invention, there is provided a process for producing a trifluoromethylbenzylamine represented by the general formula (1). This process comprises reducing an oxime represented by the general formula (2),

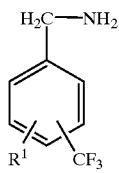
(1)

where $R^1$ represents hydrogen atom, a halogen atom selected from the group consisting of fluorine, chlorine, bromine and iodine, or trifluoromethyl group,

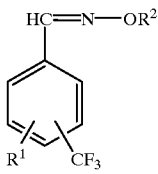
(2)

where $R^1$ is defined as above, and $R^2$ represents hydrogen atom, an alkyl group or an aralkyl group. This oxime can be obtained by reacting a trifluoromethylbenzaldehyde represented by the general formula (3) with a hydroxylamine represented by the general formula (4),

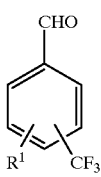
(3)

where $R^1$ is defined as above,

$H_2NOR^2$ (4)

where R2 is defined as above.

According to the process of the present invention, it becomes possible to produce the trifluoromethylbenzylamine at high yield and high selectivity, while also allowing each reaction step to be carried out under mild conditions. Therefore, this process is very effective in producing the target product in an industrial scale.

DESCRIPTION OF THE PREFERRED EMBODIMENTS

The oxime represented by the general formula (2) can produced by the first step of reacting a trifluoromethylbenzaldehyde represented by the general formula (3) with a hydroxylamine represented by the general formula (4). As stated above, the trifluoromethylbenzaldehyde is represented by the general formula (3) in which $R^1$ is hydrogen atom, a halogen atom selected from fluorine, chlorine, bromine and iodine, or trifluoromethyl group. Examples of the trifluoromethylbenzaldehyde, represented by the general formula (3), include 2-trifluoromethylbenzaldehyde, 3-trifluoromethylbenzaldehyde, 4-trifluoromethylbenzaldehyde, 3-fluoro-4-trifluoromethylbenzaldehyde, 2-fluoro-5-trifluoromethylbenzaldehyde, 2-chloro-3-trifluoromethylbenzaldehyde, 2-chloro-5-trifluoromethylbenzaldehyde, 4-chloro-3-trifluoromethylbenzaldehyde, 3,5-bis(trifluoromethyl)benzaldehyde, 2,4-bis(trifluoromethyl)benzaldehyde, 2,6-bis(trifluoromethyl)benzaldehyde and 2,5-bis(trifluoromethyl)benzaldehyde.

As stated above, the hydroxylamine is represented by the general formula (4) in which $R^2$ is hydrogen atom, an alkyl group or an aralkyl group. Specific examples of the hydroxylamine are alkylhydroxylamines having 1 to 10 carbon atoms, such as hydroxylamine, O-methylhydroxylamine, O-ethylhydroxylamine, O-propylhydroxylamine, O-isopropylhydroxylamine, O-n-butylhydroxylamines, O-isobutylhydroxylamine, O-amylhydroxylamine, O-hexylhydroxylamine, O-heptylhydroxylamine, O-octylhydroxylamine, O-2-ethylhexylhydroxylamine, O-nonylhydroxylamine and O-decylhydroxylamine. Further specific examples of the hydroxylamine are aralkylhydroxylamines such as O-benzylhydroxylamine, O-p-tolylmethylhydroxylamine and O-phenethylhydroxylamine.

In the first step of the process, the hydroxylamine may be an acid salt of hydroxylamine, and this acid salt is formed by a reaction of the hydroxylamine with an acid such as hydrochloric acid, sulfuric acid, or a carboxylic acid. In the case of using an acid salt of the hydroxylamine, a hydroxylamine obtained by neutralizing in advance the acid salt with a base may be used in the first step. Alternatively, an acid salt of the hydroxylamine may be reacted with a trifluoromethylbenzaldehyde represented by the general formula (3) in the presence of a base, resulting in generation of a hydroxylamine, while simultaneously allowing a reaction of this hydroxylamine with the trifluoromethylbenzaldehyde, thereby obtaining an oxime represented by the general formula (2). The base used in the process is preferably the one inert in the reaction. Preferable examples of the base that can be used include organic bases such as pyridine, triethylamine and N-methylmorpholine, and inorganic bases such as sodium bicarbonate, sodium carbonate, potassium bicarbonate, potassium carbonate, calcium carbonate, lithium hydroxide, sodium hydroxide and potassium hydroxide. The amount of the base used in the process is preferably at least 1 mole, and more preferably 1 to 10 moles, per mol of an acid salt of the hydroxylamine.

In the first step of the process, any solvent that is inert in the reaction can be used. Examples of solvents that can be used in the first step include ether-based, alcohol-based, amide-based, nitrile-based, aliphatic hydrocarbon-based, aromatic hydrocarbon-based, amine-based and halogenated hydrocarbon-based solvents. Typical examples of these solvents include tetrahydrofuran, diethyl ether, methanol, ethanol, dimethylformnamide, acetonitrile, hexane, benzene, toluene, pyridine, triethylamine, chloroform, methylene chloride and chlorobenzene, and two or more of these solvents can be used in combination.

The reaction temperature is normally −20 to 150° C., and although there are no particular restrictions on this temperature, the reaction proceeds smoothly even in the vicinity of room temperature.

The oxime represented by the general formula (2) is obtained nearly quantitatively from the reaction mixture obtained in the reaction of the first step by procedures such as extraction, liquid separation, concentration, distillation and crystallization. In some cases, the oxime may be able to be used in the next step (second step) while still in the form of the reaction mixture without being isolated. Furthermore, although there are two types of isomers present in the oxime obtained by the first step, that is, the syn form and anti form, the oxime can be used either in the form of a single isomer or as a mixture of both isomers in the second step of the present invention.

Next, the following provides an explanation of the second step of the process in which the trifluoromethylbenzylamine represented by the general formula (1), the final target product, is obtained by reduction of the oxime represented by the general formula (2).

In the second step, the reaction product (oxime) obtained by the first step can be reduced by catalytic hydrogenation. Although both heterogeneous and homogeneous catalysts can be used as the catalyst of the catalytic hydrogenation, heterogeneous catalysts are preferable in consideration of their ease of removal. Thus, metals or metal oxides such as palladium or platinum oxide, or these supported on a carrier such as activated carbon, alumina or diatomaceous earth, can be used. Examples of the catalyst include palladium-loaded activated carbon, palladium hydroxide-loaded activated carbon, palladium-loaded barium sulfate, palladium-loaded calcium carbonate, palladium-loaded strontium carbonate, palladium black, palladium-loaded silica gel, platinum dioxide, platinum-loaded activated carbon, platinum black, Raney nickel, ruthenium-loaded activated carbon and rhodium-loaded activated carbon. Although the amount of the catalyst may vary according to its type, it is preferably 0.0001–1 mol %, more preferably 0.001–0.1 mol %, based on the number of moles of the oxime.

Examples of the reaction solvent used in the second step include alcohols, ethers, carboxylic acids, esters, amides and water. Typical examples of these solvents include methanol, ethanol, tetrahydrofuran, diethyl ether, acetic acid, ethyl acetate and dimethylformamide, and two or more types of these solvents can be used in combination.

Hydrogen pressure for conducting catalytic hydrogenation of the second step may vary according to the solvent type, the catalyst type and other conditions. Although a pressure within the range of normal pressure (atmospheric pressure) to about 100 atmospheres can be used, a pressure of 5 atmospheres or more is used preferably.

In the second step, although a temperature within the range of −10° C. to the boiling point of the solvent can be normally used for the reaction temperature, a temperature of roughly 0–50° C. is preferable, and the object of the second step can be sufficiently achieved even at room temperature from 10–30° C.

In the second step, an acid such as hydrogen chloride, hydrogen bromide, hydrogen iodide, hydrogen fluoride, sulfuric acid or phosphoric acid can be added to the reaction system to improve the selectivity of the reaction to obtain the trifluoromethylbenzylamine represented by the general formula (1). This acid can be added to the reaction system by dissolving in water or reaction solvent. The amount of this acid is preferably 1–10 moles, and more preferably 3–5 moles, to 1 mole of the oxime represented by the general formula (2).

After separating the catalyst from the reaction mixture obtained by the reaction of the second step, the trifluoromethylbenzylamine represented by the general formula (1) can be obtained at an extremely high yield by a procedure such as concentration.

As shown in the general formula (1), the target compound, trifluoromethylbenzylamine, has an amino group at the benzyl position. It is generally known that an amino group at the benzyl position tends to be eliminated by the occurrence of hydrogenolysis by catalytic hydrogenation. Therefore, there was also concern over elimination of the amino group in the target compound of the present invention as well. However, according to the present invention, the elimination reaction of the amino group unexpectedly hardly occurs at all, and the target compound can be obtained both selectively and at significantly high yield.

The hydrogenation reaction of the oxime compound of the second step is believed to go through a reaction intermediate (5) as shown in the following reaction scheme.

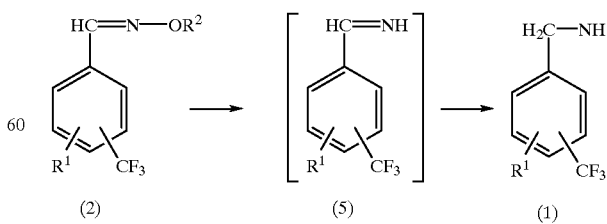

Similar to the oxime represented by the general formula (2), since this reaction intermediate (5) has one or two trifluoromethyl groups, which are extremely powerful electron attracting groups, on the benzene ring, electron density of the carbon at the benzyl position is extremely low, and is susceptible to attack by various nucleophiles such as water and the target compound of the present invention. There was therefore concern over decreased selectivity for the target compound. However, according to the process of the present invention, there is unexpectedly hardly any formation of reaction by-products such as addition products, and the target compound represented by the general formula (1) can be obtained both selectively and at remarkably high yield.

Examples of the trifluoromethlylbenzylanmine represented by the general formula (1) include 2-trifluoromethylbenzylamine, 3-trifluoromethylbenzylamine, 4-trifluoromethylbenzylamine, 3-fluoro-4-trifluoromethylbenzylamine, 2-fluoro-5-trifluoromethylbenzylamine, 2-chloro-3-trifluoromethylbenzylamine, 2-chloro-5-trifluoromethylbenzylamine, 4-chloro-3-trifluoromethylbenzylamine, 3,5-bis(trifluoromethyl)benzylamine, 2,4-bis(trifluoromethyl)benzylamine, 2,6-bis(trifluoromethyl)benzylamine and 2,5-bis(trifluoromethyl)benzylamine.

The following nonlimitative examples are illustrative of the present invention.

EXAMPLE 1

The second step of the process of the present invention was conducted as follows. At first, 5.03 g (19.6 mol) of 3,5-bis(trifluoromethyl)benzaldehyde oxime were dissolved in methanol followed by the addition of 3.0 g (82.3 mmol) of hydrogen chloride gas and 252 mg of a catalyst (i.e., activated carbon carrying thereon 5% palladium) and stirring for 5.5 hours in a hydrogen atmosphere at 10 atm and room temperature (approx. 25° C.). After removing the catalyst, ether was added to the reaction liquid, and the reaction liquid was neutralized with aqueous sodium hydroxide solution. As a result of analyzing the separated ether layer by gas chromatography, 3,5-bis(trifluoromethyl)benzylamine was formed at a yield of 94.2%.

EXAMPLE 2

The first and second steps of the process of the present invention were conducted as follows. At first, 8.79 g (50.5 mmol) of 4-trifluoromethylbenzaldehyde and 3.83 g (55.1 mmol) of hydroxylamine hydrochloride were dissolved in 12.5 ml of ethanol and 34 ml of water followed by the addition of 2,5 g of sodium hydroxide and stirring for 1 hour at room temperature. After adding ether and washing with dilute hydrochloric acid, the reaction liquid was further washed with saturated brine followed by drying with mirabilite and concentrating to obtain 9.25 g (48.2 mmol) of 4-trifluoromethylbenzylaldehyde oxime (yield: 95.5%). 5.00 g (26.4 mmol) of this 4-trifluoromethylbenzaldehyde oxime were dissolved in methanol followed by the addition of 4.0 g (109.7 mmol) of hydrogen chloride gas and 252 mg of the same catalyst as that of Example 1 and stirring for 3 hours in a hydrogen atmosphere at 10 atm and room temperature (approx. 250° C.). After removing the catalyst, ether was added to the reaction liquid, and the reaction liquid was neutralized with aqueous sodium hydroxide solution. As a result of analyzing the separated ether layer by gas chromatography, 4-trifluoromethylbenzylamine was formed at a yield of 93.6%.

What is claimed is:

1. A process for producing a trifluoromethylbenzylamine represented by the general formula (1)

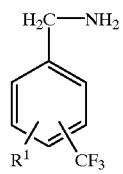

(1)

where $R^1$ represents a hydrogen atom, a halogen atom selected from the group consisting of fluorine, chlorine, bromine and iodine, or trifluoromethyl group, said process comprising reducing an oxime represented by the general formula (2)

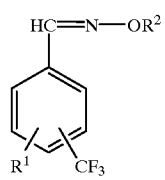

(2)

where $R^1$ is defined as above, and $R^2$ represents hydrogen atom, an alkyl group or an aralkyl group, by a catalytic hydrogenation of said oxime in the presence of a catalyst, in a reaction solvent containing an acid.

2. A process according to claim 1, wherein said catalyst is a heterogeneous catalyst.

3. A process according to claim 2, wherein said heterogeneous catalyst is an activated carbon carrying thereon palladium.

4. A process according to claim 1, wherein said catalyst is in an amount of 0.0001 to 1 mol %, based on the number of moles of said oxime.

5. A process according to claim 1, wherein said catalytic hydrogenation is conducted under a hydrogen pressure of 5 atmospheres or more.

6. A process according to claim 1, wherein said acid is hydrogen chloride.

7. A process according to claim 1, wherein said acid is in an amount of 1–10 moles per mol of said oxime.

8. A process for producing a trifluoromethylbenzylamine represented by the general formula (1)

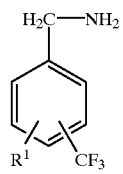

(1)

where $R^1$ represents hydrogen atom, a halogen atom selected from the group consisting of fluorine, chlorine, bromine and iodine, or trifluoromethyl group, said process comprising:

(a) reacting a tritluoromethylbenzaldehyde represented by the general formula (3)

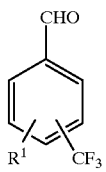

(3)

where $R^1$ is defined as above, with a hydroxylamine represented by the general formula (4)

$H_2NOR^2$ (4)

where $R^2$ represents hydrogen atom, an alkyl group or an aralkyl group, thereby obtaining an oxime represented by the general formula (2)

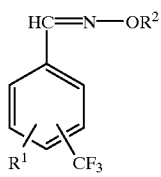

(2)

where $R^1$ and $R^2$ are defined as above, and (b) reducing said oxime by a catalytic hydrogenation thereof in the presence of a catalyst in a reaction solvent containing an acid, thereby producing said trifluoromethylbenzylamine.

9. A process according to claim 8, wherein said hydroxylamine is prepared by neutralizing an acid salt of said hydroxylamine with a base.

10. A process according to claim 9, wherein said base is selected from the group consisting of pyridine, triethylamine, N-methylmorpholine, sodium bicarbonate, sodium carbonate, potassium bicarbonate, potassium carbonate, calcium carbonate, lithium hydroxide, sodium hydroxide, and potassium hydroxide.

11. A process according to claim 9, wherein a molar ratio of said base to said acid salt of said hydroxylamine is at least 1.

12. A process according to claim 8, wherein said trifluoromethylbenzaldehyde is selected from the group consisting of 2-trifluoromethylbenzaldehyde,
3-trifluoromethylbenzaldehyde,
4-trifluoromethylbenzaldehyde,
3-fluoro-4-trifluoromethylbenzaldehyde,
2-fluoro-5-trifluoromethylbenzaldehyde,
2-chloro-3-trifluoromethylbenzaldehyde,
2-chloro-5-trifluoromethylbenzaldehyde,
4-chloro-3-trifluoromethylbenzaldehyde,
3,5-bis(trifluoromethyl)benzaldehyde,
2,4-bis(trifluoromethyl)benzaldehyde,
2,6-bis(trifluoromethyl)benzaldehyde, and
2,5-bis(trifluoromethyl)benzaldehyde;

and wherein said trifluoromethylbenzylamine is selected from the group consisting of 2-trifluoromethylbenzylamine,
3-trifluoromethylbenzylamine,
4-trifluoromethylbenzylamine,
3-fluoro-4-trifluoromethylbenzylamine,
2-fluoro-5-trifluoromethylbenzylamine,
2-chloro-3-trifluoromethylbenzylamine,
2-chloro-5-trifluoromethylbenzylamine,
4-chloro-3-trifluoromethylbenzylamine,
3,5-bis(trifluoromethyl)benzylamine,
2,4-bis(trifluoromethyl)benzylamine,
2,6-bis(trifluoromethyl)benzylamine, and
2,5-bis(trifluoromethyl)benzylamine.

13. A process for producing a trifluoromethylbenzylamine represented by the general formula (1)

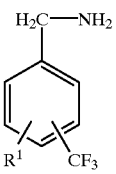

(1)

where $R^1$ represents hydrogen atom, a halogen atom selected from the group consisting of fluorine, chlorine, bromine and iodine, or trifluoromethyl group, said process comprising:

(a) mixing together
a trifluoromethylbenzaldehyde represented by the general formula (3)

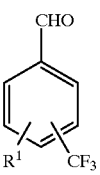

(3)

where $R^1$ is defined as above,
an acid salt of a hydroxylamine represented by the general formula (4)

$H_2NOR^2$ (4)

where $R^2$ represents hydrogen atom, an alkyl group or an aralkyl group, and a base, thereby obtaining an oxime represented by the general formula (2)

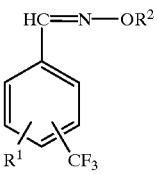

(2)

where $R^1$ and $R^2$ are defined as above, and (b) reducing said oxime by a catalytic hydrogenation of said oxime in the presence of a catalyst in a reaction solvent containing an acid, thereby producing said trifluoromethylbenzylamine.

* * * * *